US009579648B2

(12) United States Patent
Marshall et al.

(10) Patent No.: US 9,579,648 B2
(45) Date of Patent: Feb. 28, 2017

(54) CUVETTE ASSEMBLY HAVING CHAMBERS FOR CONTAINING SAMPLES TO BE EVALUATED THROUGH OPTICAL MEASUREMENT

(71) Applicant: BacterioScan Inc., St. Louis, MO (US)

(72) Inventors: Dana A. Marshall, St. Louis, MO (US); Theodore S. McMinn, St. Louis, MO (US); Dan Vadim Regelman, Kiryat Bialik (IL)

(73) Assignee: BacterioScan LTD, MP Western Galilee (IL)

( * ) Notice: Subject to any disclaimer, the term of this patent is extended or adjusted under 35 U.S.C. 154(b) by 0 days.

(21) Appl. No.: 14/562,304

(22) Filed: Dec. 5, 2014

(65) Prior Publication Data

US 2015/0160119 A1   Jun. 11, 2015

Related U.S. Application Data

(60) Provisional application No. 61/912,763, filed on Dec. 6, 2013.

(51) Int. Cl.
*B01L 3/00*       (2006.01)
*G01N 21/51*      (2006.01)

(52) U.S. Cl.
CPC .......... *B01L 3/50255* (2013.01); *G01N 21/51* (2013.01); *B01L 2200/0684* (2013.01);
(Continued)

(58) Field of Classification Search
CPC ........................... G01N 21/03; B01L 3/50255
(Continued)

(56) References Cited

U.S. PATENT DOCUMENTS 3,627,424 A    12/1971 Dorman et al.
3,713,775 A *   1/1973 Schmitz ................ B01L 3/5021
                                                    206/223
(Continued)

FOREIGN PATENT DOCUMENTS

DE          10128978       12/2002
EP           0320154        6/1989
(Continued)

OTHER PUBLICATIONS

Murray, et al. "Light-scattering methods for antibiotic sensitivity tests", J Clin Pathol, 1980, vol. 33, pp. 995-1001, 8 pages.
(Continued)

*Primary Examiner* — Jill Warden
*Assistant Examiner* — Dwayne K Handy
(74) *Attorney, Agent, or Firm* — Nixon Peabody LLP

(57) ABSTRACT

The present invention is a cuvette assembly for use in optically measuring at least one characteristic of particles within a plurality of liquid samples. The cuvette assembly comprises a main body having internal walls and external walls, and a plurality of cuvettes within the main body at least partially being defined by the internal walls. Each of the plurality of cuvettes has a liquid-input chamber for receiving a respective one of the plurality of liquid samples, a filter, and an optical chamber for receiving a respective filtered liquid sample caused by passing the respective one of the plurality of liquid samples through the filter. Each of the optical chambers includes an entry window for allowing transmission of an input light beam through the filtered liquid sample and an exit window for transmitting a forward scatter signal caused by the particles within the filtered liquid sample.

26 Claims, 7 Drawing Sheets

(52) U.S. Cl.
CPC ... *B01L 2300/022* (2013.01); *B01L 2300/043* (2013.01); *B01L 2300/044* (2013.01); *B01L 2300/045* (2013.01); *B01L 2300/0672* (2013.01); *B01L 2300/0681* (2013.01); *B01L 2400/0683* (2013.01); *G01N 2021/513* (2013.01)

(58) Field of Classification Search
USPC ........................................................ 422/554
See application file for complete search history.

(56) References Cited

U.S. PATENT DOCUMENTS

| | | | |
|---|---|---|---|
| 3,832,532 | A | 8/1974 | Praglin et al. |
| 3,928,140 | A | 12/1975 | Wyatt et al. |
| 4,066,360 | A | 1/1978 | Breddin et al. |
| 4,101,383 | A | 7/1978 | Wyatt et al. |
| 4,113,386 | A | 9/1978 | Lepper, Jr. |
| 4,119,407 | A * | 10/1978 | Goldstein ............. G01N 21/07 422/413 |
| 4,265,538 | A | 5/1981 | Wertheimer |
| 4,577,970 | A | 3/1986 | Meserol |
| 4,754,613 | A | 7/1988 | Brito |
| 4,874,102 | A * | 10/1989 | Jessop ................. B01L 3/50825 215/273 |
| 4,895,446 | A | 1/1990 | Maldari et al. |
| 5,139,031 | A | 8/1992 | Guirguis |
| 5,187,368 | A | 2/1993 | Galante et al. |
| 5,212,667 | A | 5/1993 | Tomlinson, Jr. et al. |
| 5,351,118 | A | 9/1994 | Spinell |
| 5,616,923 | A | 4/1997 | Rich et al. |
| 5,693,944 | A | 12/1997 | Rich |
| 5,969,814 | A * | 10/1999 | Barber ................. G01N 21/253 356/338 |
| 5,989,499 | A * | 11/1999 | Catanzariti ............ B01L 3/502 422/417 |
| 6,091,483 | A | 7/2000 | Guirguis |
| 6,230,045 | B1 | 5/2001 | Hoogenraad et al. |
| 6,333,008 | B1 | 12/2001 | Leistner et al. |
| 6,573,992 | B1 | 6/2003 | Drake |
| 6,861,230 | B1 | 3/2005 | Murphy et al. |
| 7,430,046 | B2 | 9/2008 | Jiang et al. |
| 7,961,311 | B2 | 6/2011 | Weichselbaum et al. |
| 8,339,601 | B2 | 12/2012 | Weichselbaum et al. |
| 2003/0048433 | A1 | 3/2003 | Desjonqueres |
| 2004/0070756 | A1 | 4/2004 | Rastopov |
| 2004/0185552 | A1 | 9/2004 | Griner et al. |
| 2004/0238746 | A1 | 12/2004 | Dreyer et al. |
| 2005/0148085 | A1 | 7/2005 | Larsen |
| 2006/0063146 | A1 | 3/2006 | Larsen et al. |
| 2006/0109476 | A1 | 5/2006 | Werner et al. |
| 2006/0256338 | A1 | 11/2006 | Gratton et al. |
| 2007/0155017 | A1 | 7/2007 | Wyatt |
| 2007/0159619 | A1 | 7/2007 | Chu et al. |
| 2007/0195324 | A1 | 8/2007 | Adams et al. |
| 2007/0206203 | A1 | 9/2007 | Trainer |
| 2007/0211251 | A1 | 9/2007 | Weischselbaum |
| 2007/0253042 | A1 | 11/2007 | Szarvas |
| 2008/0106737 | A1 | 5/2008 | Weichselbaum et al. |
| 2008/0293091 | A1 | 11/2008 | Kanipayor |
| 2010/0277734 | A1 | 11/2010 | Weichselbaum |
| 2013/0089476 | A1 | 4/2013 | Weichselbaum et al. |

FOREIGN PATENT DOCUMENTS

| | | |
|---|---|---|
| EP | 1136563 | 9/2001 |
| GB | 1515681 | 6/1978 |
| GB | 2412166 | 9/2005 |
| WO | WO 00/09981 | 2/2000 |
| WO | WO 00/66763 | 11/2000 |
| WO | WO 2006/018839 | 2/2006 |
| WO | WO 2013/070948 A1 | 5/2013 |
| WO | WO 2013/153371 A1 | 10/2013 |

OTHER PUBLICATIONS

PCT International Search Report and Written Opinion of the International Search Authority regarding PCT/IL2006/01379, mailed Jul. 11, 2008, 8 pages.
International Search Report, PCT/US14/68564, 4 pages, date of mailing Apr. 16, 2015.
International Written Opinion, PCT/US14/68564, 6 pages, date of mailing Apr. 16, 2015.
International Preliminary Report on Patentability, PCT/US14/68564, mailed Nov. 2, 2015, 7 pages.

* cited by examiner

CUVETTE ASSEMBLY HAVING CHAMBERS FOR CONTAINING SAMPLES TO BE EVALUATED THROUGH OPTICAL MEASUREMENT

RELATED APPLICATIONS

The present application claims priority to U.S. Provisional Application Ser. No. 61/912,763, filed Dec. 6, 2013, titled "Multi-Cuvette," which is herein incorporated by reference in entirety.

COPYRIGHT

A portion of the disclosure of this patent document may contain material which is subject to copyright protection. The copyright owner has no objection to the facsimile reproduction by anyone of the patent disclosure, as it appears in the Patent and Trademark Office patent files or records, but otherwise reserves all copyright rights whatsoever.

FIELD OF THE INVENTION

The present invention relates generally to the field of optical measurements of contained liquid samples. Specifically, the present invention relates to a cuvette assembly having multiple chambers for containing samples, such as liquid samples, that will be evaluated by optical measurements through windows associated with the chambers.

BACKGROUND OF THE INVENTION

Many applications in the field of analytical research and clinical testing utilize optical methods for analyzing liquid samples. Among those methods are absorbance, turbidity, fluorescence/luminescence, and optical scattering measurements. Optical laser scattering is one of the most sensitive methods, but its implementation can be very challenging, especially when analyzing biological samples in which suspended particles are relatively transparent in the medium. In this case, most of the scattering process occurs in the forward direction near the incident laser beam. To detect this forward scattering signal, high extinction of the incident beam is required.

One particle that often requires evaluation within a liquid is bacteria. The presence of bacteria is often checked with biological liquids, such as urine, amniotic, pleural, peritoneal and spinal liquids. In a common analytical method, culturing of the bacteria can be time-consuming and involve the use of bacterial-growth plates placed within incubators. Normally, laboratory results take several days to determine whether the subject liquid is infected with bacteria.

In some systems, cuvettes have been used to receive liquid samples that are then subjected to the optical measurement by transmission of an input beam through the cuvette and observation of the forward scatter signals. These devices have been used relative to the detection of bacteria within the liquid. However, the cuvettes are not conducive to mass production for commercial use. Nor do these prior art cuvettes have user friendly features that permit for ease of use by operators. Furthermore, these prior art cuvettes lack mechanisms that permit the easy flow of the liquid sample into the optical chamber through a filter.

Accordingly, there is a need for an improved cuvette that is easy to mass produce, permits easy use by the operator, and more readily delivers the liquid sample into the optical chamber through the filter.

SUMMARY OF THE INVENTION

The present invention is a cuvette assembly for use in optically measuring at least one characteristic of particles within a plurality of liquid samples. The cuvette assembly comprises a main body having internal walls and external walls, and a plurality of cuvettes within the main body are at least partially defined by the internal walls. Each of the plurality of cuvettes has a liquid-input chamber for receiving a respective one of the plurality of liquid samples, a filter, and an optical chamber for receiving a respective filtered liquid sample caused by passing the respective one of the plurality of liquid samples through the filter. Each of the optical chambers includes an entry window for allowing transmission of an input light beam through the filtered liquid sample and an exit window for transmitting a forward scatter signal caused by the particles within the filtered liquid sample.

In another aspect, the present invention involves a cuvette assembly for use in optically measuring at least one characteristic of particles within a plurality of liquid samples. The cuvette assembly includes a main body having a plurality of openings. Each opening is for receiving a respective one of the plurality of liquid samples. Each of the plurality of openings leads to an associated liquid-input chamber that is in fluidic communication with an associated optical chamber. Each optical chamber has an entry window for allowing transmission of an input light beam through the respective liquid sample and an exit window for transmitting a forward scatter signal caused by the particles within the respective liquid sample. The cuvette assembly further includes a plurality of individual closure mechanisms. Each of the plurality of closure mechanisms is associated with a respective one of the plurality of openings. Each of the plurality of closure mechanisms is movable from an initial opened position for receiving the respective liquid sample to a closed position that inhibits leakage from the associated liquid-input chamber.

In a further aspect, the present invention is a cuvette assembly for use in optically measuring at least one characteristic of particles within a plurality of liquid samples. The cuvette assembly includes a main body having internal walls that at least partially define a plurality of optical chambers for receiving a respective one of the plurality of liquid samples. Each of the optical chambers includes an entry window for allowing transmission of an input light beam through the respective liquid sample and an exit window for transmitting an optical signal caused by the particles within the respective liquid sample. The main body further including a lower surface that is at an angle relative to a central axis of the input light beam. A first pair of registration structures is associated with the angled lower surface of the main body. The first pair of registration structures is intended to mate with a corresponding pair of registration features on a platform in an instrument associated with a light source producing the input light beam.

In yet a further aspect, the present invention is a cuvette assembly for use in optically measuring at least one characteristic of particles within a plurality of liquid samples. The cuvette assembly comprises a plurality of cuvettes. Each of the plurality of cuvettes has a liquid-input chamber for receiving a respective one of the plurality of liquid samples, a filter, and an optical chamber for receiving a respective filtered liquid sample from the filter. Each optical chamber includes a vent for allowing displaced gas to escape as the filtered liquid sample enters the optical chamber.

In yet another aspect, the present invention is a cuvette assembly for use in optically measuring at least one characteristic of particles within a plurality of liquid samples. The cuvette assembly comprises a plurality of cuvettes. Each of the plurality of cuvettes has a liquid-input chamber for receiving a respective one of the plurality of liquid samples, a filter, and an optical chamber for receiving a respective filtered liquid sample from the filter. The cuvette assembly includes ports to receive applied pressure to the liquid samples within the liquid-input chamber so as to force the samples through the filters and into the optical chambers. Or, the cuvette assembly includes port(s) associated with the optical chamber to apply a suction force (or a vacuum) to draw the filtered liquid sample through the filter and into the optical chamber.

In another aspect, the present invention is a cuvette assembly for use in optically measuring at least one characteristic of particles within a plurality of liquid samples. The cuvette assembly comprises a plurality of cuvettes within a main body of the cuvette assembly. Each of the plurality of cuvettes has a liquid-input chamber for receiving a respective one of the plurality of liquid samples and an optical chamber for receiving a respective liquid sample from the associated liquid-input chamber. Each of the optical chambers includes an entry window for allowing transmission of an input light beam through the liquid sample and an exit window for transmitting an optical signal caused by the particles within the liquid sample. At least one window assembly is attached to the main body that includes either (i) all of the entry windows for the plurality of optical chambers or (ii) all of the exit windows for the plurality of optical chambers.

In another aspect, the present invention is a cuvette assembly for use in optically measuring at least one characteristic of particles within a plurality of liquid samples. The cuvette assembly comprises a plurality of cuvettes. Each of the plurality of cuvettes has a liquid-input chamber for receiving a respective one of the plurality of liquid samples and an optical chamber for receiving a respective liquid sample from the associated liquid-input chamber. Each of the optical chambers includes an entry window for allowing transmission of an input light beam through the liquid sample and an exit window for transmitting an optical signal caused by the particles within the liquid sample. Each cuvette is preloaded with one or more chemo-effectors for mixing with liquid sample located therein.

Additional aspects of the invention will be apparent to those of ordinary skill in the art in view of the detailed description of various embodiments, which is made with reference to the drawings, a brief description of which is provided below.

Figure 1:
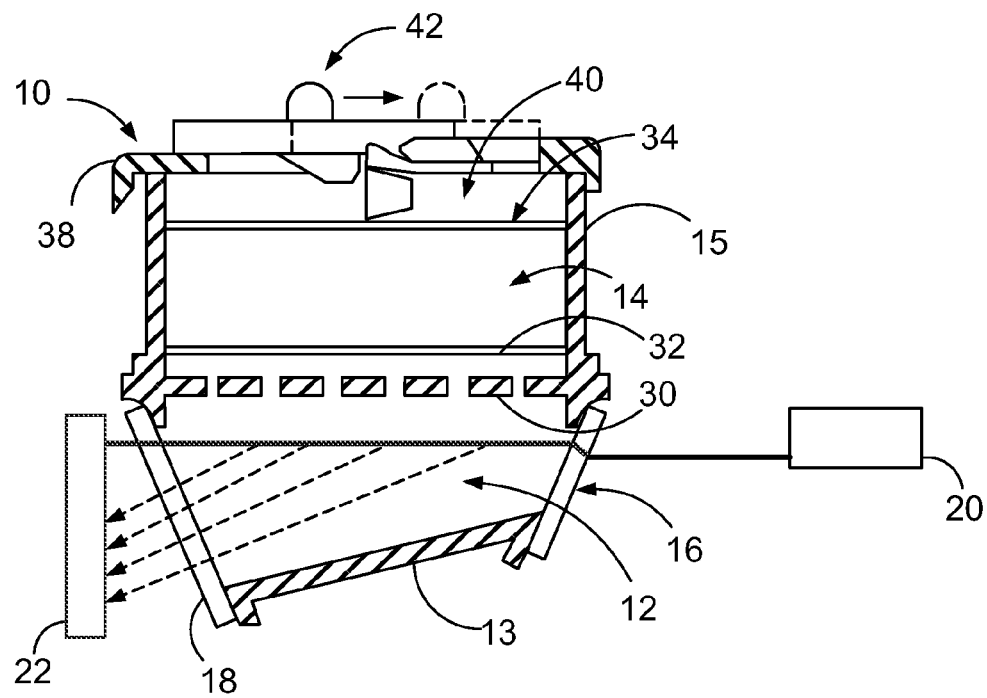
FIG. 1 schematically illustrates a sectional view through the liquid-input chamber and optical chamber of one cuvette of a cuvette assembly in accordance with the present invention.

While the invention is susceptible to various modifications and alternative forms, specific embodiments will be shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

The drawings will herein be described in detail with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation."

Figure 2:
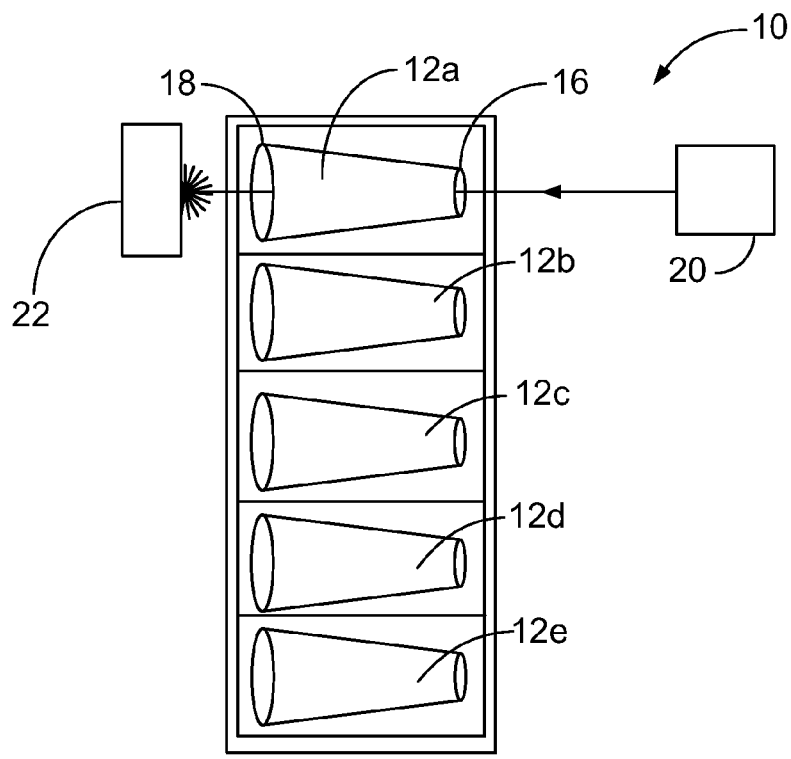
FIG. 2 is a top plan view of the cuvette assembly of FIG. 1.

FIGS. 1 and 2 schematically illustrate a first embodiment of the cuvette assembly 10 according to the present invention. As shown in FIG. 2, the cuvette assembly 10 includes five optical chambers 12a, 12b, 12c, 12d, 12e defined by internal and external walls on a lower portion 13 of the main body of the cuvette assembly 10. As illustrated in FIG. 1, a liquid-input chamber 14 is located above each optical chamber 12 and is also defined by internal and external walls on the upper portion 15 of the main body of the cuvette assembly 10. Each liquid-input chamber 14 and its associated optical chamber 12 form an individual cuvette. The cuvette assembly 10 is preferably made of plastic material, such as polycarbonate, polystyrene, or ABS, and is preferably disposable.

The optical chamber 12 of the cuvette assembly 10 includes an entry window 16 and an exit window 18. A light source 20, such as a laser, provides an input beam (solid line) that passes from the entry window 16, through a liquid sample within the optical chamber 12, and through the exit window 18. When the liquid sample includes particles, a forward scattering signal (dashed lines) is produced by the impingement of the input beam on the particles within the liquid sample and is detected by a sensor 22. The forward scattering signal provides characteristics (e.g., quantity, size, or concentration) of the particles present in the liquid sample, which is useful for diagnostic applications, medical applications, non-medical applications, and research applications. In one particularly useful application, the particles are bacteria, which can be detected and counted by various techniques that are generally described in U.S. Pat. Nos. 7,961,311 and 8,339,601, both of which are commonly owned and are herein incorporated by reference in their entireties.

As seen in FIGS. 1-2, the optical chamber 12 within the lower portion 13 of the main body has angled walls in the horizontal and vertical planes. The angled walls provide an optical chamber that is roughly conic with a smaller entry window 16 than the exit window 18 so that light can spread from the entry window 16 without impinging on the walls. In one embodiment, the opposing angled walls are within 12° to 16° of parallel to the input beam (i.e., each vertical wall and horizontal wall is within about 6° to 8° of a central axis of the optical chamber 12). Also, angled "light traps" might be incorporated into the angled walls of the optical chamber 12 to trap, absorb, and/or contain interior light reflections from the windows 16, 18 or wall surfaces.

The windows 16, 18 at each end of the optical chamber 12 are transparent to the input beam. The windows 16, 18 are thin (less than 1 mm) and are tipped at an angle to ensure that the surfaces of the windows 16, 18 are not normal to the input beam so as to reduce retro-reflections that might interfere with the measurement of the forward scattering signal at the sensor 22. The windows 16, 18 can be angled in the same or different planes. The windows 16, 18 can be glass or plastic, and can also be a plastic film. They must have low surface roughness (preferably a surface microroughness less than 100 angstroms rms) and minimum inclusions that would produce scatter, which could also interfere with the measurement of the forward scattering signal at the sensor 22.

Regarding the transfer of the liquid sample from the upper portion 15 to the lower portion 13 of the cuvette assembly 10, the liquid sample is initially located within the liquid-input chamber 14 and is then passed through a filter 32 (e.g., a permeable membrane 32) into the optical chamber 12. The filter 32 removes particles of a particular size, for example excluding particles larger than bacteria by filtering to below about 0.01 mm (about 10 microns), leaving only certain sized particles present in the filtered liquid sample located in the optical chamber 12. An intermediate partition 30 within the cuvette assembly 10 supports the filter 32 and includes a group of openings that permit the filtered liquid sample to pass from the liquid-input chamber 14 into the optical chamber 12. Alternatively, the intermediate partition 30 may have openings that are sized and shaped to provide enough filtering so as to avoid the need for the additional filter 32.

The cuvette assembly 10 may also include a foil or frangible membrane 34 (or one-use frangible feature) below an opening 40 on the upper structure 38 of the main body to seal the interior of the liquid-input chamber 14 before use of the cuvette assembly 10. The foil or frangible membrane 34 could be pierced or displaced by a standard pipette, syringe tip, sharp cannula, or other tube that injects the liquid sample into the liquid-input chamber 14. This foil or frangible membrane 34 serves to protect the integrity or sterility of the interior of the liquid-input chamber 14 and the optical chamber 12 prior to use, and also provides tamper-evidence or use-evidence for a user. The frangible membrane 32 could also be a resilient or rubber material so that it could be pierced by a sharp cannula, but still retain the liquid sample inside the liquid-input chamber 14 and below the frangible membrane 32 after being pierced. Several mechanisms exist for blunt cannula access (such as those mechanisms used in needleless infusion devices) might be incorporated to allow transfer of the liquid sample into the interior of the liquid-input chamber 14. For example, these mechanisms may include a slideable or deformable rubber element mounted in a tubular body, with a slit or opening in the element that is forced open by being displaced by a syringe luer taper. They may also include a spring-loaded valve poppet or moveable element that can be displaced from a sealing ring by being displaced by a blunt cannula, or a "duck-bill" collapsed rubber tube that can be forced open by a blunt cannula.

The intermediate partition 30 may also help to form a vent (not shown in FIGS. 1-2) from the optical chamber 12 to the upper region of the liquid-input chamber 14 to facilitate venting air (or other gas) that is displaced from the optical chamber 12 upon receipt of the filtered liquid sample. There may also be a feature to connect this vent through a wall of the liquid-input chamber 14 to an apparatus outside the cuvette assembly 10 for applying a vacuum to the optical chamber 12 to promote liquid moving through the filter membrane 32 and/or intermediate partition 30, which is shown in more detail in FIG. 9. This vent may be small (e.g., less than 3 mm diameter, or less than 1 mm) or include a restrictive section or aperture so that fluid pulled by vacuum through the vent encounters substantial flow resistance (back pressure), which can be detected by the vacuum apparatus to indicate that the optical chamber 12 is filled and to cease applying the vacuum. Once the filtered liquid sample is within the optical chamber 12, the optical measurements associated with the light source 20 and the sensor 22 may be initiated.

To maintain liquid samples within the cuvette assembly 10 after they have been introduced into the liquid-input chambers 14 via the openings 40, a closure mechanism 42 is associated with each of the liquid-input chambers 14 of the cuvette assembly 10. The closure mechanism 42 is preferably a single-use sliding closure that preferably provides a locking feature after it is moved from an initial opened position (solid lines) to a closed position (dashed lines). The sliding closure mechanism 42 could have a ratchet or pall device incorporated therein to lock it in the closed position on the upper structure 38 so that the cuvette assembly 10 is assured of only a single use. The sliding closure mechanism 42 also served as evidence of use. The sliding closure mechanism 42 preferably includes a wiping feature to ensure a liquid-tight closure that inhibits or precludes leakage of liquid from the liquid-input chamber 14. The sliding closure mechanism 42 and associated wiping feature also ensure that exterior contaminants cannot be introduced into the liquid-input chamber 14 after the sliding closure mechanism 42 is in the closed position. Furthermore, the sliding closure mechanism 42 preferably has a configuration that is tailored to fit a pipette or loading tube to preclude liquid or gas leaking around the tube, or to wipe the end of the tube as it is withdrawn from the opening 40. Alternatively, the closure mechanism 42 can be a hinged closure with a locking pall or snap feature, which also serves to ensure a single use and also as evidence of use. The hinged closure mechanism is also preferably liquid-tight when closed.

Figure 3:
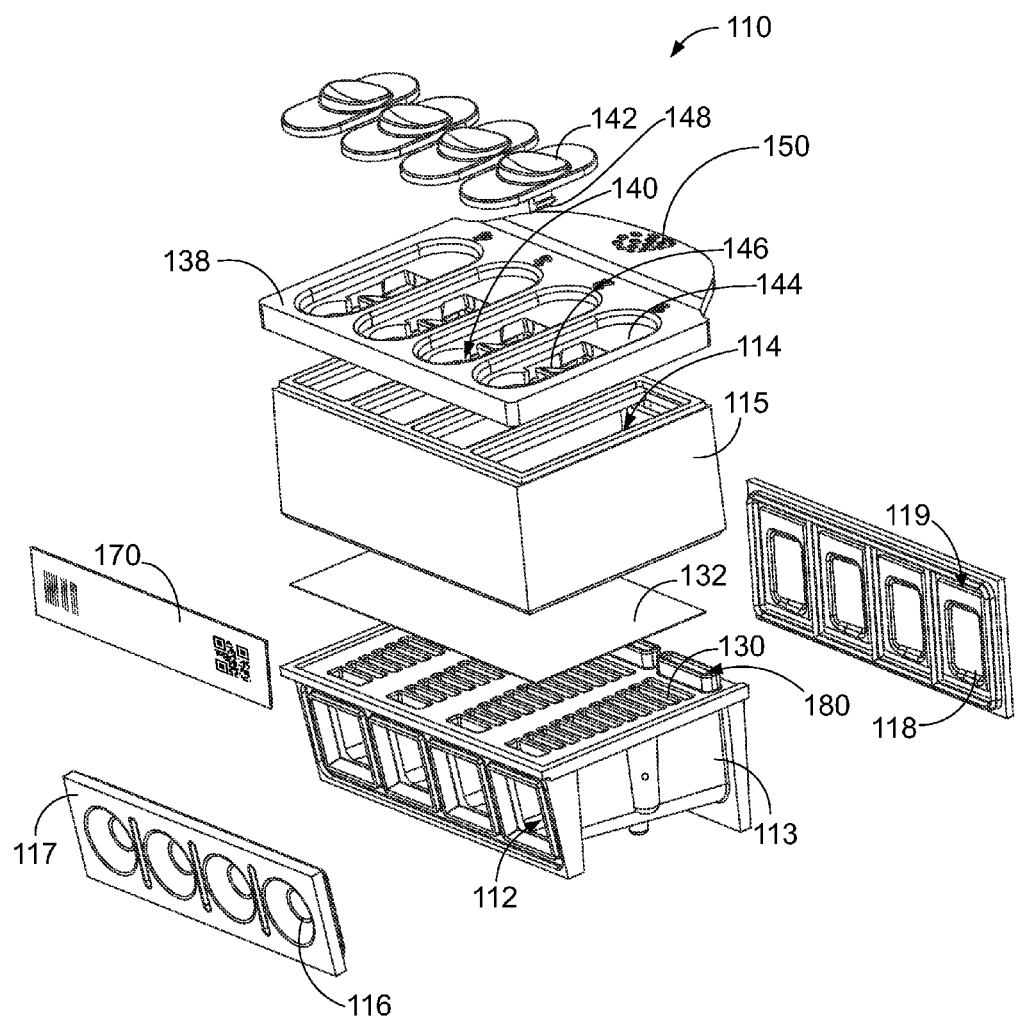
FIG. 3 is an exploded view of another embodiment of a cuvette assembly having multiple chambers in accordance with the present invention.
Figure 4:
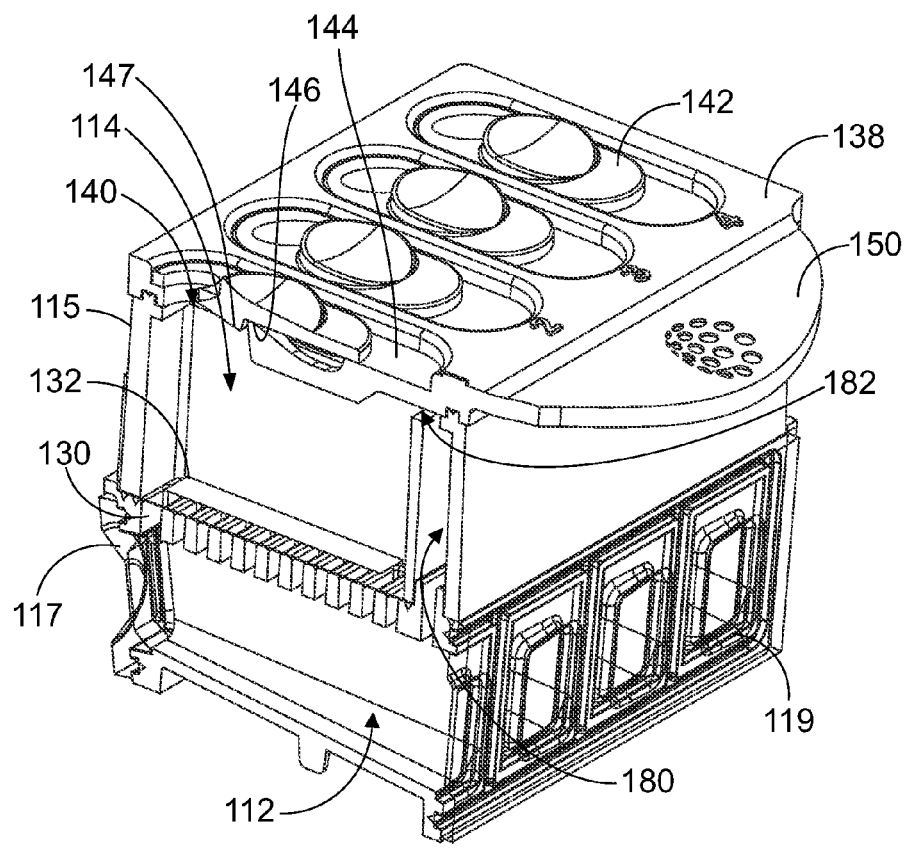
FIG. 4 is a perspective view of a cuvette assembly of FIG. 3 with the first optical chamber and associated liquid-input chamber illustrated in a sectional view.

FIGS. 3-7 illustrate another embodiment of a cuvette assembly 110 that is similar to the cuvette assembly 10 of FIGS. 1-2, where similar structures are now referenced with 100-series reference numerals. Referring initially to FIGS. 3-4, the cuvette assembly 110 includes four separate cuvettes, each of which includes an optical chamber 112 and a liquid-input chamber 114. As with the previous embodiments, the internal and external walls of the lower portion 113 of the main body of the cuvette assembly 110 define the optical chamber 112. For example, the first optical chamber 112 is partially defined by the side external wall, an internal wall, and a bottom wall of the lower portion 113, as well as the entry and exit windows 116, 118. The associated liquid-input chamber 114 is partially defined by a side external wall, an internal wall, and a pair of front and back external walls on the upper portion 115 of the main body of the cuvette assembly 110.

Each of the four entry windows 116 is a part of an entry window assembly 117 that is attached to the lower portion 113 of the main body of the cuvette assembly 110. Similarly, each of the four exit windows 118 is part of an exit window assembly 119 that is attached to the lower portion of the main body opposite the entry window assembly 117. In other words, the present invention contemplates a single unitary optical structure that provides the transmission of the input beam into all four respective optical chambers 112, and a single unitary optical structure that provides for the exit of the forward scattering signals from the respective optical chambers 112. The lower portion 113 of the main body includes structural recesses that mate with the corresponding structures on the window assemblies 117, 119 for registering them in a proper orientation during assembly of the cuvette assembly 110.

An intermediate partition 130 within the cuvette assembly 110 separates the lower portion 113 defining the four optical chambers 112 from the upper portion 115 defining the liquid-input chambers 114. The intermediate partition 130, which is shown as being part of the lower portion 113 (although it could be part of the upper portion 115), includes four separate groups of openings that permit the flow of liquid from the liquid-input chamber 114 into the associated optical chamber 112. The openings can be a variety of shapes that permit the flow of the liquid. As shown, the openings progressively get longer moving from the entry window 116 to the exit window 118 because the shape of the optical chamber 112 increases in area in the same direction. Additionally, the filter 132 rests upon the intermediate partition 130, such that the same filter 132 is used for each of the four regions. When the same filter 132 is used for all four regions, the interior walls of the upper portion 115 must provide adequate pressure at the filter 132 to prevent crossing fluid flows through the filter 132 between adjacent liquid-input chambers 112. In a further alternative, no filter 132 is present because the intermediate partition 130 includes adequate sized openings to provide the necessary filtering of the liquid sample, or because the liquid samples are pre-filtered before entering each liquid-input chamber 114.

To provide the initial introduction of the liquid samples into the cuvette assembly 110, the upper structure 138, which is attached to the upper portion 115 of the main body of the cuvette assembly 110, includes four openings 140 corresponding to the four liquid-input chambers 114. Four sliding mechanisms 142 are located within four corresponding grooves 144 on the upper structure 138 and are initially placed in an opened position such that the openings 140 are initially accessible to the user for introducing the liquid samples. Each of the sliding mechanisms 142 includes a pair of projections 148 that engage corresponding side channels at the edges of each of the corresponding grooves 144 to permit the sliding action. Within each groove 144, there is a latching ramp 146 over which the sliding mechanism 142 is moved when transitioning to its closed position. A corresponding latch 147 (FIG. 4) on the underside of the sliding mechanism 142 moves over the latching ramp 146 and creates a locking mechanism when the sliding mechanism 142 has been fully moved to the closed position. The upper structure 138 of the cuvette assembly 110 also includes a gripping handle 150 that permits the user to easily grasp the cuvette assembly 110 during transport to and from an instrument that incorporates the light source 20 and the sensor 22.

To help seal the cuvette assembly 110 after the liquid samples have been placed within the respective liquid-input chambers 114, the periphery of the sliding mechanism 142 adjacent to the opening 140 can be configured to tightly mate with the walls defining the groove 144 (or undercut channels within the groove 144) to inhibit any leakage around the opening 140 in the upper structure 138. Alternatively, a resilient plug-like structure can be located on the underside of the sliding mechanism 142 that fits within the opening 142 create a seal and inhibit leakage. Or, a gasket can be provided around the opening 140 to provide a sealing effect on the underside of the sliding mechanism 142.

The upper portion 115 and the lower portion 113 of the main body of the cuvette assembly 110 can be attached to each other through various techniques, such as ultrasonic welding, thermal welding, with adhesive, or through interfering snap-fit connections. Similarly, the upper structure 138 can be attached to the upper portion 115 of the main body through similar techniques. And, the window assemblies 117, 119 can be attached to the lower portion 113 through the same attachment techniques. The width dimension of the overall cuvette assembly 110 across the four cuvettes is roughly 4 cm. The length dimension of the overall cuvette assembly 110 (i.e., parallel to the input beam) is approximately 2 cm. The height dimension of the overall cuvette assembly 110 is approximately 2 cm, such that each of the liquid input chambers 114 is approximately 1 cm in height and each of the optical chambers 112 is approximately 1 cm in height (although the optical chambers 112 have a varying height along the length direction due to their conical shape). In some embodiments, each optical chamber 112 is designed to contain approximately 1.2 to 1.5 cubic centimeters (i.e., approximately 1.2 to 1.5 ml) of a fluid sample. Each liquid-input chamber 114 is designed to hold slightly more of the liquid sample (e.g., 1.7 to 2.5 ml), which is then fed into the corresponding optical chamber 112.

Because each of the cuvette assemblies 110 may be used for different applications, the cuvette assembly 110 may use barcodes or RFID tags to identify the type of test supported by the particular cuvette assembly 110, as well as other measurement data to be taken. The instrument that includes the light source 20 and the sensor 110 preferably reads the RFID or barcode, and selects the software to run the appropriate optical measurement tests on the cuvette assembly 110. Accordingly, the cuvette assembly 110 preferably includes an identification label 170, which may include barcodes and/or quick response codes ("QR-code") that provide the necessary coded information for the cuvette assembly 110. Other codes can be used as well. Specifically, when bacteria is a particle being checked within the liquid sample, one of the codes on the label 170 may provide the protocol for the test (e.g., temperature profile over duration of test, frequency of the optical measurements, duration of test, etc.). Another one of the codes may be associated with information on the patient(s) from whom the liquid samples were taken, which may include some level of encryption to ensure that patient data is kept confidential. Another code may provide a quality-assurance check of the part number or the serial number for the cuvette assembly 110 to ensure that the cuvette assembly 110 is an authentic and genuine part, such that improper cuvettes are not tested. The code for the quality-assurance check may also prevent a cuvette assembly 110 from being tested a second time (perhaps after some type of cleaning) if it is intended for only single use.

The cuvette assembly 110 also includes a vent 180 that extends from the optical chamber 112 into the upper portion 115 of the main body the cuvette assembly 110. The vent 180 includes a chimney-like portion that extends upwardly from the intermediate partition 130. The chimney-like portion is then received in a channel in the upper portion 115, which extends to an opening 182 leading into the liquid-input chamber 114 just below the upper structure 138 that defines the upper boundary of the liquid-input chamber 114. Accordingly, the gas (e.g., air) that is initially present in the optical chamber 112 can be readily displaced as the optical chamber 112 receives the filtered liquid sample from the liquid-input chamber 114 (via the filter 132). The vent 180 can also lead to the external environment on the outside of the cuvette assembly 110.

Figure 5:
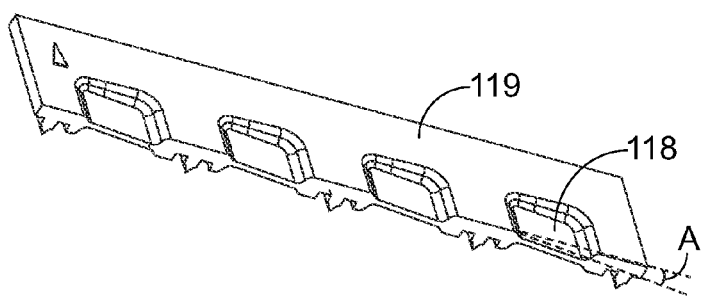
FIG. 5 is a cross-sectional view through the exit window assembly taken along line 5-5 of FIG. 7.
Figure 7:
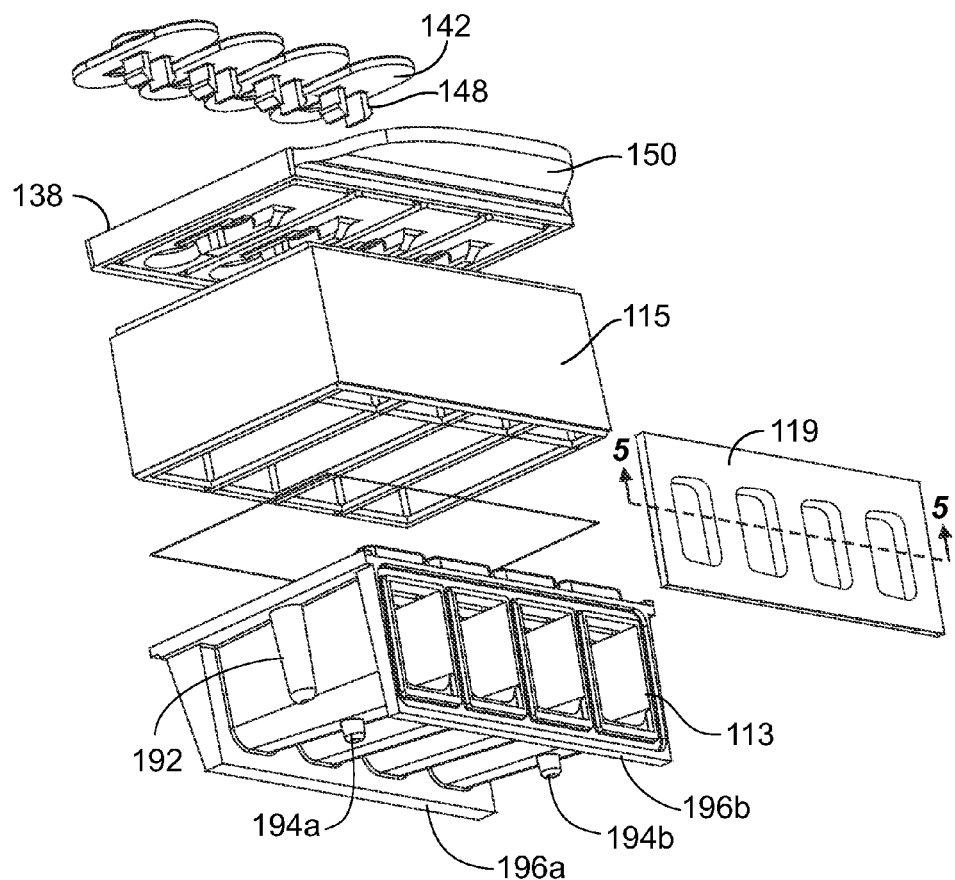
FIG. 7 is an exploded view of the cuvette assembly of FIG. 4 showing the various alignment and registration features at the bottom of the cuvette assembly.

FIG. 5 illustrates a cross-section taken along line 5-5 of the exit window assembly 119 in FIG. 7. The exit window assembly 119 includes the four exit windows 118 for the four optical chambers 112. To help minimize reflections from the input beam as it impinges on each surface of each exit window 118, each of the exit windows 118 is angled relative to the central axis of the input beam by an angle "A." The angle "A" is preferably about 5°, but can range from about 2° degrees to about 15°.

Figure 6:
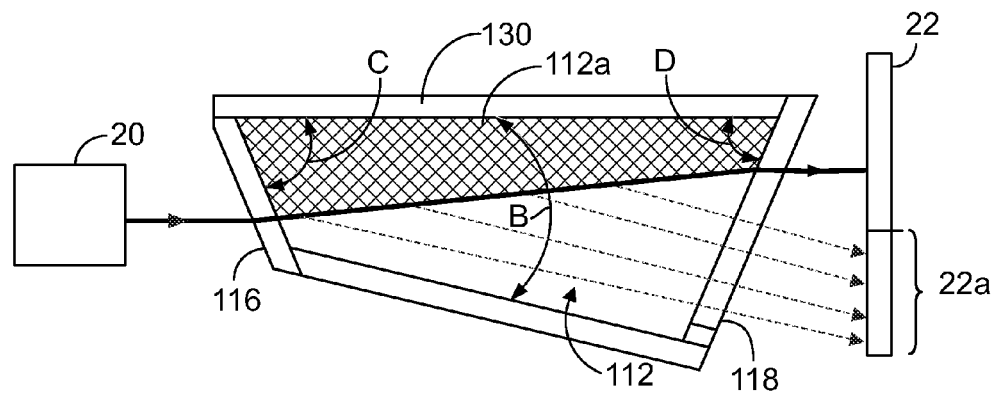
FIG. 6 is a schematic view of one optical chamber of the cuvette assembly of FIG. 3 in response to an input beam being transmitted through the entry window.

FIG. 6 schematically illustrates the effects of the input beam within the optical chamber 112 of the cuvette assembly 110, as well as the geometry of the optical chamber 112. In particular, the light source 20 provides an input beam that is transmitted towards the entry window 116. The entry window 116 is tilted at an angle relative to the input beam such that the input beam refracts upwardly toward the intermediate partition 130 of the cuvette assembly 110. As the input beam passes through the liquid sample within the optical chamber 112, a forward scatter signal (dashed lines) is produced due to the input beam impinging upon particles within the liquid sample. Due to various reflections and optical scatter, the upper portion 112a of the optical chamber 112 becomes an irrelevant region for optical measurement. Only the forward scatter signal that is received by the lower portion 22a of the sensor 22 is relevant to determining the characteristics (e.g., quantity, size, and/or concentration) of the particles present within liquid sample in the optical chamber 112. As mentioned previously, the optical chamber 112 is conical with the angle "B" that provides for expansion of the cross-sectional area of the optical chamber 112 in the direction of the exit window 118. The angle "B" is in the range of about 12° to 16°.

Preferably, each of the entry windows 116 and the exit windows 118 meets the intermediate partition 130 at acute interior angles "C" and "D", respectively. Assuming the input beam from the light source 20 is substantially parallel to the intermediate partition 130, the acute interior angles help to reduce the reflections that would otherwise interfere with the forward scatter signal that is received at the lower portion 22a of the sensor 22. For example, angle "C" may be roughly 85° such that the input beam impinges upon the entry window 116 at an angle of approximately 85° so as to refract upward slightly, while providing minimal internal reflections toward the lower portion 22a of the sensor 22. Similarly, angle "D" for the exit window 118 is roughly 89° so as to again minimize the internal reflections that could be received at the lower portion 22a the sensor 22, while maximizing the amount of forward scatter signal that can be received at the lower portion 22a the sensor 22. And, as noted above relative to FIG. 5, the exit window 118 is also angled in the opposing place as well. In summary, the optical chamber 112 and the windows 116, 118 are configured to maximize the amount of forward scatter signal that is received by the lower portion 22a of the sensor 22, while minimizing the amount of internal reflections that could be received in the lower region 22a of the sensor 22. Furthermore, it should be noted that the input beam, which has a much higher intensity than the forward scatter signal, can be blocked or attenuated by a beam dump after leaving the exit window 118 to reduce or eliminate the transmission of the input beam signal at the sensor 22.

Figure 8:
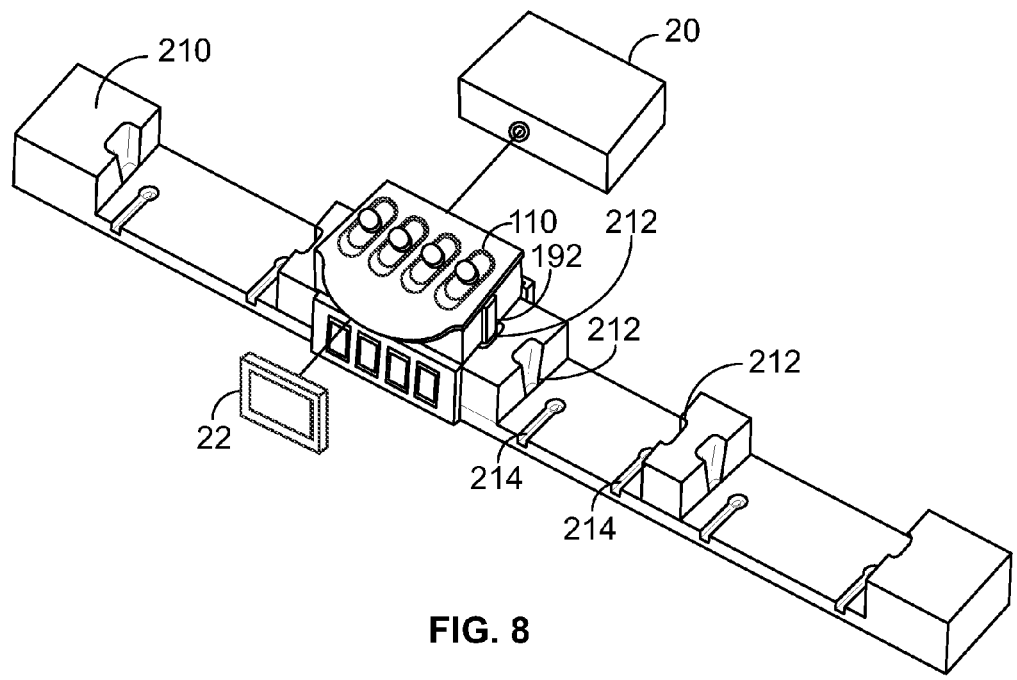
FIG. 8 illustrates the cuvette assembly of FIG. 4 registered on a platform that is typically located within an optical measurement instrument.

Referring now to FIGS. 7-8, the cuvette assembly 110 also includes different types of registration features to allow the cuvette assembly 110 to be located properly on a registration platform 210 (FIG. 8) within the instrument that is used for the optical measurements. In particular, the cuvette assembly 110 includes a pair of side registration features 192 located on the lower portion 113 of the cuvette assembly 110. Further, the cuvette assembly 110 includes lower registration features 194a and 194b on a lower surface of the lower portion 113 of the cuvette assembly 110. Finally, lower segments of the front and back walls 196a and 196b extending downwardly from the lower surface also serve as registration features for the cuvette assembly 110.

With reference to FIG. 8, the side registration features 192 undergo sliding engagement within corresponding vertical grooves 212 on pillars associated with the registration platform 210. Additionally, lower registration features 194a and 194b can slide within horizontal grooves 214 on an upper surface of the registration platform 210. The horizontal grooves 214 terminate in openings that receive the lower registration features 194a and 194b (illustrated as projections) on the cuvette assembly 110. Finally, the distance between the lower segments of the front and back walls 196a and 196b corresponds to the width of the registration platform 210 such that cuvette assembly 110 becomes nestled between adjacent pillars with the front and back walls 196a and 196b overlying the front and back edges of the registration platform 210.

As can be seen best in FIGS. 4 and 6, the lower surface of the lower portion 113 of the cuvette assembly 110, which includes the lower registration features 194a and 194b, is at angle relative to the upper structure 138 of the cuvette assembly 110 and to the input beam from the light source 20 due to the conical geometry of the optical chamber 112. Accordingly, the upper surface of the registration platform 210 is angled in an opposing manner that allows the input beam to be generally horizontal (and generally parallel to the upper structure 138 of the cuvette assembly 110) when the cuvette assembly 110 is placed on the registration platform 210. It should be noted, however, that the cuvette assembly 110 can be properly registered on the registration platform 210 with less than these three distinct registration features illustrated in FIGS. 7-8.

Once the cuvette assembly 110 is nestled properly on the registration platform 210, the light source 20 can sequentially transmit the input beam through each of the four optical chambers 112 of the cuvette assembly 110 and the forward scatter signal associated with the particles within each of the liquid samples can be sequentially received by the sensor 22. For example, the light source 20 and sensor 22 can be controllably indexed between positions to receive optical measurements taken in adjacent optical chambers 112. As can be seen in FIG. 8, each platform 210 is capable of receiving four cuvette assemblies 110, such that optical measurements can be taken from sixteen different liquid samples within the four cuvette assemblies 110 nestled on the registration platform 210.

Figure 9:
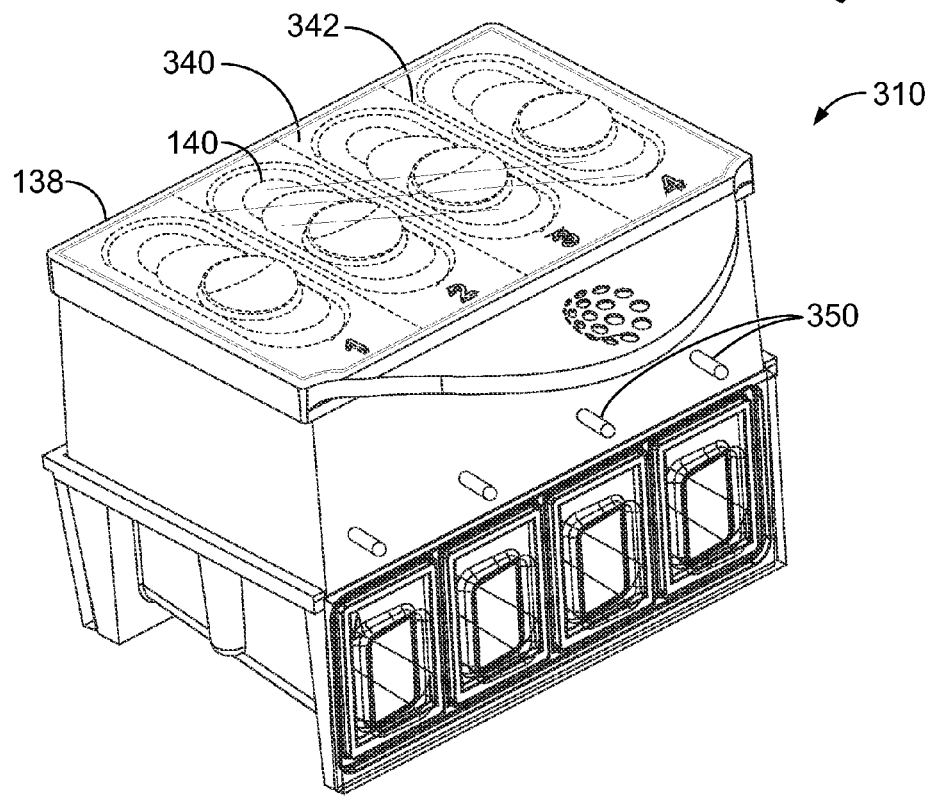
FIG. 9 illustrates a cuvette assembly having a contamination-prevention film located over the upper structure of the cuvette assembly.

FIG. 9 illustrates an alternative cuvette assembly 310, which is slightly different from the embodiments previously illustrated. In particular, the cuvette assembly 310 includes a thin film 340 located over the upper structure 138 and the sliding mechanisms associated with the openings on the upper structure 138. The thin film 340 provides an extra layer of protection to ensure no contamination enters the openings when the sliding mechanisms located under the film 340 are in their open positions prior to use. Once the user has chosen to use the cuvette assembly 310, he or she tears the thin film 340 from the upper structure 138 and places the four liquid samples into each of the four liquid-input chambers 114. Alternatively, the film 340 may have multiple perforations 342 to allow for the removal of four distinct thin films over the four openings.

Additionally, FIG. 9 illustrates four vacuum ports 350 that provide access to the four interior vacuum channels, each of which is associated with a respective one of the optical chambers 112. The interior vacuum channels are similar in structure to the vents 180 in FIG. 4, except they do not have the upper openings 182, thereby causing a draw of gas (e.g., air) only within the optical chambers 112. Because some types of liquid samples may not easily pass through the filter 132, applying a lower pressure to the four vacuum ports 350 serves to draw the liquid sample through the filter 132 and into the optical chamber 112. The cuvette assembly 310 may be placed on a vacuum or suctioning platform (similar to the registration platform 210 in FIG. 8) and a corresponding set of aligned tubes or a longer manifold can overlie the vacuum ports 350 to automatically apply the negative pressure, thereby resulting in the liquid sample being pulled through the filters 132 into the corresponding optical chambers 112. Other manual methods for applying the negative pressure to the vacuum ports 350 can be used as well.

Figure 10:
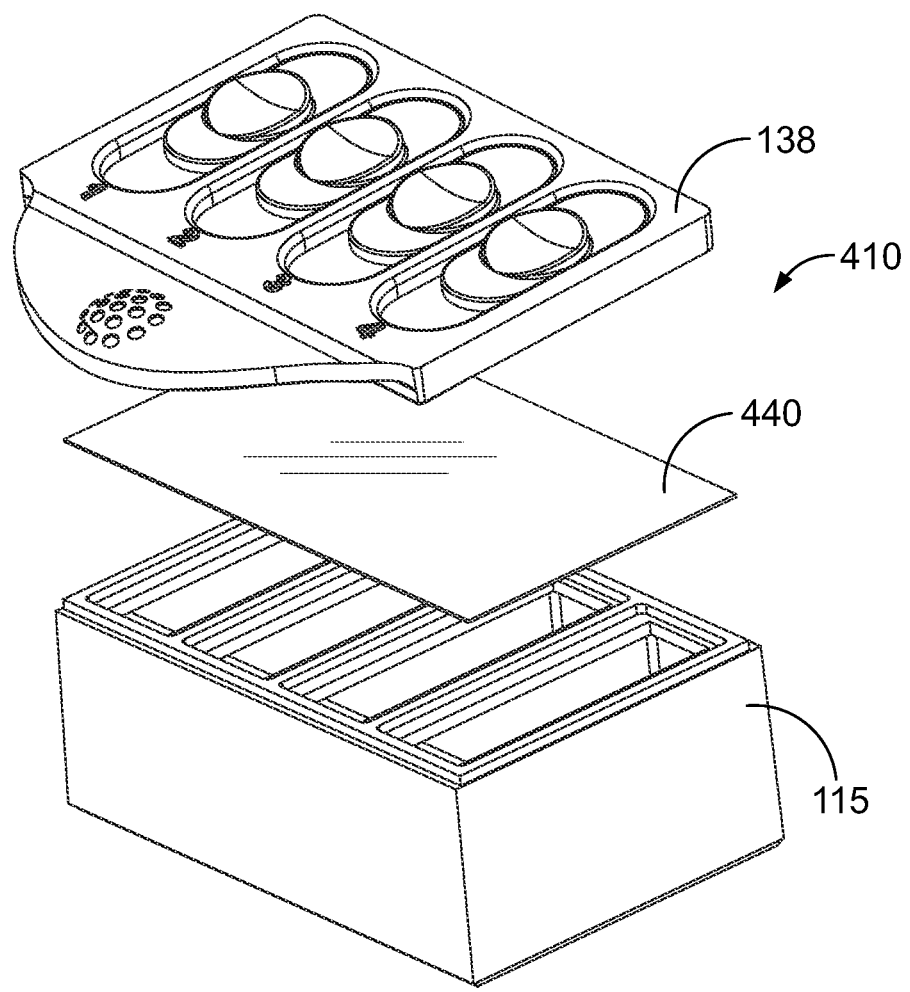
FIG. 10 illustrates yet another embodiment of the cuvette assembly according to the present invention that includes a frangible film directly below the openings of the cuvette assembly.

FIG. 10 illustrates another alternative cuvette assembly 410 having a membrane 440 directly below the openings on the upper structure 138. The membrane 440 could be pierced or displaced by a standard pipette, syringe tip, sharp cannula, or other tube that injects the liquid sample into the liquid-input chamber 114. This membrane 440 serves to protect the integrity and/or sterility of the interior of the liquid-input chambers 114 within the upper portion 115 of the main body, and also the optical chamber 112 prior to use. It further provides tamper-evidence or use-evidence for a user. The membrane 440 could also be resilient or rubber material so that it could be pierced by a sharp cannula, and still retain the interior liquid sample within the liquid-input chamber 114 after the sharp cannula is refracted. Furthermore, to the extent that the liquid-input chamber 114 is depressurized so as to help draw the liquid sample into the liquid-input chamber 114, the membrane 440 can seal the liquid-input chamber 114 to maintain a pressure lower than the ambient environment (or maintain a vacuum) within the liquid-input chamber 114.

The interior of the liquid-input chamber 114 of the cuvette assembly 410 could be manufactured under a vacuum, or could contain a lyophilized material, such as an antibiotic or some other chemo-effector. If manufactured under a vacuum, piercing the frangible membrane 440 with a pipette or cannula would apply this vacuum to the pipette or cannula and, thus, draw the contents into the liquid-input chamber 114. Similarly, the frangible membrane 440 and permeable filter membrane 132 (FIG. 3-4) can be configured so that a vacuum in the cuvette assembly 410 would draw deposited liquid samples through the permeable filter membrane 132 for filtration of the liquid sample and/or for exposure of the liquid sample to a chemical coating (e.g., chemo-effector) on the permeable filter membrane 132.

In an alternative embodiment of FIG. 10, a lower frangible membrane or seal could be incorporated below the permeable filter membrane 132. A mechanical feature can then pierce this lower frangible membrane by user action, such as by the loading pipette or a separate tool, by flexing of devices in the cuvette body, or by the motion of the sliding or hinged closure mechanisms. As an example, the lower surface of the permeable filter membrane 132 directly adjacent to the lower frangible membrane can have a plurality of projecting features that, when forced downwardly, cause the lower frangible membrane to be pierced. In this alternative, the optical chamber 112 and fluid input chamber 114 are isolated until this lower frangible membrane is pierced or displaced. The lower optical chamber 112 could be in a vacuum (or other low pressure state) compared with the liquid-input chamber 114, and piercing this membrane could serve to apply the vacuum to the lower face of the permeable filter membrane 132 and, thus, draw flow of the liquid sample through the permeable filter membrane 132.

Figure 11:
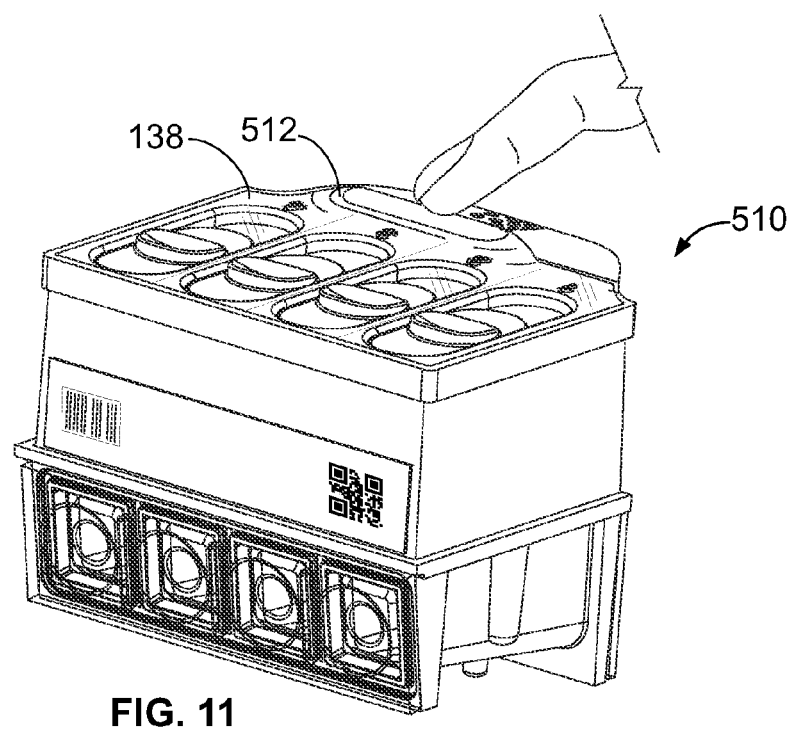
FIG. 11 illustrates yet a further embodiment of the cuvette assembly according to the present invention that includes a manual pump to help force a liquid within the upper liquid-input chamber through a filter so that it enters the lower optical chamber.

FIG. 11 illustrates another alternative cuvette assembly 510 having a manual pump 512 on the upper structure 138 of the cuvette assembly 510. The manual pump 512 can be actuated by the user by pushing downwardly to force a volume of air within the cuvette assembly 510 to be forced onto the sample liquids that have been placed in the four liquid-input chambers 114. After the sliding mechanisms 142 (FIGS. 3-4) have been moved to the closed position, thereby providing some sealing effect around the openings 140, the user actuates the manual pump 512, which causes the sample liquids to be forced downwardly through the filter 132 and into the optical chamber. Again, like the suctioning effect from the vacuum ports 350 in FIG. 9, providing a pressure differential across the filter 132 enhances the flow of the sample liquid from the fluid input chamber 114, through the filter 132, and into the optical chamber 112. While one common manual pump 512 is disclosed, the present invention contemplates a single manual pump for each of the liquid-input chambers 114. Of course, an automatic pump can also apply pressure to the liquid samples through ports in the upper portion of the cuvette assembly 510.

Figure 12:
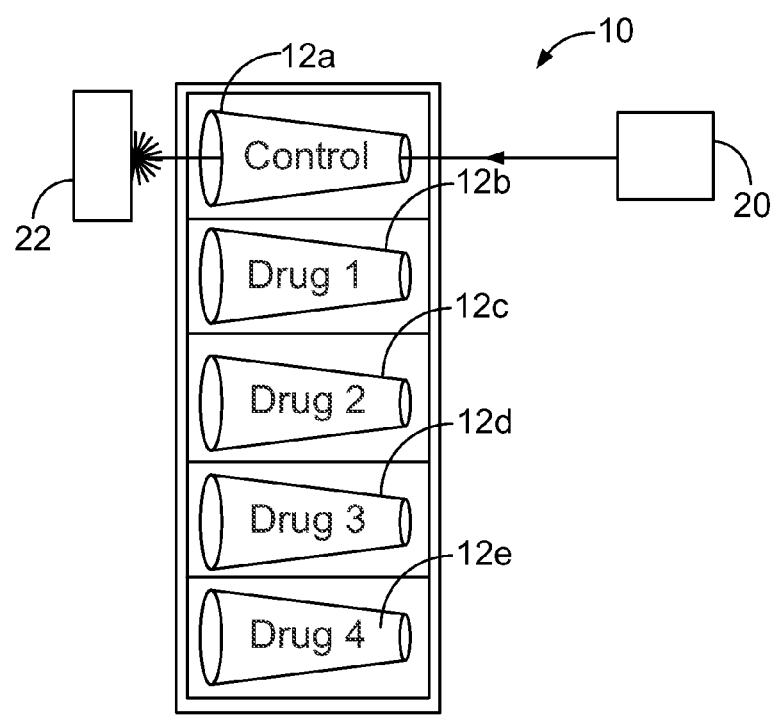
FIG. 12 schematically illustrates one application for the cuvette assemblies according to the present invention in which a single cuvette assembly contains a control sample and four different drug samples, or a control sample and four different dosages of a single drug sample.

FIG. 12 illustrates the use of the cuvette assembly 10 in one particular application. While FIG. 12 illustrates the application relative to the cuvette assembly 10 of FIGS. 1-2, the application equally applies to the cuvette assemblies 110, 310, 410 and 510 illustrated in FIGS. 3-11. In first optical chamber 12a, a liquid sample serves as a control for the test.

For example, the first optical chamber 12a may be a liquid sample from the patient having an infection (e.g., a urinary tract infection). The second optical chamber 12b may have the same patient's liquid sample, but mixed with a first drug ("Drug 1") applied thereto. Similarly, the third optical chamber 12c may have the same patient's liquid sample, but mixed with a second drug ("Drug 2"). Likewise, the fourth optical chamber 12d may have the same patient's liquid sample, but mixed with a third drug ("Drug 3"). Finally, the fifth optical chamber 12e may have the same patient's liquid sample, but mixed with a fourth drug ("Drug 4"). The cuvette assembly 10 provides for a simplistic method for determining the effect of each of the four drugs on the patient by measuring the bacterial content (bacteria particles) over a period of time. For example, the untreated control sample in the first optical chamber 12a may result in a forward scatter signal that increases due to the growth of bacteria in the untreated liquid sample. But, that same liquid sample from the patient may experience less growth in the number of bacteria when exposed to Drugs 3 and 4. And, that same liquid sample from the patient may experience no growth or a decrease in the growth in the number of bacteria when exposed to Drugs 1 and 2.

Alternatively, Drugs 1, 2, 3, and 4 can be the same type of antibiotic, but at different levels such that the cuvette assembly is useful in determining the "minimum inhibitive concentration" that is needed to reduce or retard bacterial growth. In short, each of the cuvette assemblies of the present invention are useful in determining the effects of a chemo-effector (such as an antibiotic, or a nutrient growth medium) by allowing for an easy measurement of changes in microbial growth rates for liquid samples exposed to different chemo-effectors or liquid samples exposed to the same chemo-effector, but at different concentrations.

In one particular example, the cuvette assembly 10 has a plurality of chambers that are loaded with different combinations of chemo-effectors (for example, pre-mixed sterile liquid growth media such as Luria Broth, each with a different concentration of some number of antibiotics). The user can load a small amount (e.g. 0.05 mL) of a chemo-effector sample into each liquid-input chamber 14 by piercing the membrane, depositing the sample, removing the pipette or cannula. The chemo-effector sample and liquid sample can mix, and the cuvette assembly 10 can then be measured and incubated in an instrument with the light source 20 and the sensor 22. The different rates of growth of a pathogen could be measured for each chamber that holds variable concentrations of the antibiotic, and a "minimum inhibitive concentration" can be established from these results in a short period. This may be incorporated into a cuvette assembly 10 having chambers with no chemo-effectors, or chambers that do not receive liquid samples but are simply present to provide control or calibration standards for the optical measurements associated with the light source 20 and the sensor 22. In other words, the present invention contemplates an optical chamber in the cuvette assembly as containing a control or calibration liquid.

With regard to the specific use of a chemo-effectors, a chemo-effector may be a dry (e.g., lyophilized) material, a coating on a surface of one of the chambers or on the filter, a liquid or solution, a gaseous atmosphere (such as Argon, O2, or CO2), or some combination. In the present invention, the chemo-effector is preferably pre-loaded into the cuvette assembly 10, and closed by one of the internal membranes, films, foils, or other frangible or moveable feature for future use. The chemo-effector may be a growth media combined with an antibiotic and combined with other biochemical reagents. In particular, the chemo-effector could be loaded into the fluid-input chamber 14, enclosed with a frangible membrane above it and/or below it (for example, membrane 34, filter membrane 32, 132, film 340, membrane 440, and/or a film below the filter 132 and above the intermediate partition 130) to isolate it from the optical chamber 12. The cuvette assembly 10 would permit the piercing of the frangible membranes in a sequence to provide for exposure of the chemo-effector to a loaded liquid sample, to another chemo effector, to a vacuum or gaseous environment, or to a permeable filter membrane, prior to or in the process of transferring the fluid sample to the optical chamber 14.

Each of these embodiments and obvious variations thereof is contemplated as falling within the spirit and scope of the claimed invention, which is set forth in the following claims. Moreover, the present concepts expressly include any and all combinations and subcombinations of the preceding elements and aspects.

The invention claimed is:

1. A cuvette assembly for use in optically measuring at least one characteristic of particles within a plurality of liquid samples, comprising:
    a main body having a unitary upper structure attached thereto, the unitary upper structure defining a plurality of openings, each opening for receiving a respective one of the plurality of liquid samples, each of the plurality of openings leading to an associated liquid-input chamber that is within the main body below the unitary upper structure and in fluidic communication with an associated optical chamber, each optical chamber has an entry window for allowing transmission of an input light beam through the respective liquid sample and an exit window for transmitting a forward scatter signal caused by the particles within the respective liquid sample; and
    a plurality of individual closure mechanisms located on the unitary upper structure, each of the plurality of closure mechanisms being associated with a respective one of the plurality of openings, each of the plurality of closure mechanisms being movable from an initial opened position for receiving the respective liquid sample to a closed position that inhibits leakage from the associated liquid-input chamber.

2. The cuvette assembly of claim 1, wherein each of the plurality of individual closure mechanisms is locked in the closed position to inhibit reopening of the closure mechanism.

3. The cuvette assembly of claim 1, wherein each of the plurality of closure mechanisms is slidable from the initial opened position to the closed position.

4. The cuvette assembly of claim 1, wherein each of the plurality of closure mechanisms is rotatable about a hinge to move from the initial opened position to the closed position.

5. The cuvette assembly of claim 1, further including a filter located between each of the liquid-input chambers and the associated optical chamber for filtering the respective liquid sample received by the optical chamber.

6. The cuvette assembly of claim 5, further including a vent associated with each optical chamber to permit the gas within the optical chamber to be displaced as the respective liquid sample enters the optical chamber.

7. The cuvette assembly of claim 6, wherein the vent permits the gas within the optical chamber to be displaced into the associated liquid-input chamber.

8. The cuvette assembly of claim 1, further including a frangible membrane within each of the liquid-input chambers through which a respective liquid sample is received by piercing the frangible membrane with a pointed object.

9. The cuvette assembly of claim 1, further including a contamination-prevention membrane located over the plurality of individual closure mechanisms to inhibit contamination of the liquid-input chambers via the openings when the plurality of individual closure mechanisms are in the initial opened position.

10. The cuvette assembly of claim 1, further including at least one chemo-effector that is pre-loaded into more than one of the liquid-input chambers for mixing with the respective liquid sample, the chemo-effector in one of the liquid-input chambers being different in type or concentration from the chemo-effector in at least one other liquid-input chamber.

11. A cuvette assembly for use in optically measuring at least one characteristic of particles within a plurality of liquid samples, comprising:
a main body having internal walls and external walls; and
a plurality of individual cuvettes within the main body at least partially defined by the internal and external walls, adjacent ones of the plurality of individual cuvettes being separated by a singular one of the internal walls, each of the plurality of cuvettes having a liquid-input chamber for receiving a respective one of the plurality of liquid samples, a filter, and an optical chamber for receiving a respective filtered liquid sample caused by passing the respective one of the plurality of liquid samples through the filter, each of the optical chambers including an entry window for allowing transmission of an input light beam through the filtered liquid sample and an exit window for transmitting a forward scatter signal caused by the particles within the filtered liquid sample.

12. The cuvette assembly of claim 11, further including a plurality of closure mechanisms, each of the plurality of closure mechanisms being associated with a respective one of the plurality of liquid-input chambers, each of the plurality of closure mechanisms being in an initial opened position for receiving a respective one of the plurality of liquid samples and being movable to a closed position after receipt of the respective one of the plurality of liquid samples.

13. The cuvette assembly of claim 12, wherein each of the plurality of closure mechanisms is locked in the closed position to inhibit leakage from the cuvette assembly.

14. The cuvette assembly of claim 13, wherein the main body includes an upper portion and a lower portion, the upper portion defining the plurality of liquid-input chambers, the lower portion defining the plurality of optical chambers.

15. The cuvette assembly of claim 14, further including an intermediate partition associated either with the upper portion or the lower portion, the intermediate partition having a plurality of groups of openings, each of the groups being associated with one of the liquid-input chambers and for passing the associated filtered liquid sample to the optical chamber.

16. The cuvette assembly of claim 15, wherein the groups of openings in the intermediate partition provides the filter for each cuvette.

17. The cuvette assembly of claim 11, further including a vent leading from each of the optical chambers to permit displacement of a gas from the optical chamber upon receipt of the filtered liquid sample.

18. The cuvette assembly of claim 11, further including a frangible membrane within each of the liquid-input chambers through which a respective liquid sample is received by piercing the frangible membrane with a pointed object.

19. The cuvette assembly of claim 18, wherein the pressure within the main body and below the frangible membrane is less than ambient pressure so as to draw the respective liquid sample into the liquid-input chamber.

20. The cuvette assembly of claim 11, further including a window assembly attached to the main body, the window assembly providing either all of the exit windows for the optical chambers or all of the entry windows for the optical chambers.

21. The cuvette assembly of claim 11, wherein a pressure differential is created between each of the optical chambers and the associated liquid-input chamber for urging the respective liquid sample through the filter and into the optical chamber.

22. The cuvette assembly of claim 21, wherein the pressure differential is caused by at least one of a pumping force applied to the liquid-input chambers and a suction force applied to openings associated with the optical chambers.

23. The cuvette assembly of claim 11, further including at least one chemo-effector that is pre-loaded into more than one of the liquid-input chambers for mixing with the respective liquid sample, the chemo-effector in one of the liquid-input chambers being different in type or concentration from the chemo-effector in at least one other liquid-input chamber.

24. A cuvette assembly for use in optically measuring at least one characteristic of particles within a plurality of liquid samples, comprising:
a main body having internal walls for at least partially defining a plurality of optical chambers for receiving a respective one of the plurality of liquid samples, each of the optical chambers including an entry window for allowing transmission of an input light beam through the respective liquid sample and an exit window for transmitting an optical signal caused by the particles within the respective liquid sample, the main body further including a lower surface that is at an angle relative to a central axis of the input light beam; and
a first pair of registration structures extending downwardly from the angled lower surface of the main body, the first pair of registration structures for mating with a corresponding pair of registration features on a platform in an instrument associated with a light source producing the input light beam.

25. The cuvette assembly of claim 24, wherein the optical signal is a forward scatter signal produced by the input light beam impinging on the particles.

26. The cuvette assembly of claim 24, further including a second pair of registration structures associated with the angled lower surface, the second pair of registration structures for mating with a corresponding second pair of registration features on the platform in the instrument associated with the light source producing the input light beam, the second pair of registration features including lower wall segments of the main body extending downwardly for engaging regions of the platform.

* * * * *